US005965366A

United States Patent [19]
Ochoa et al.

[11] Patent Number: 5,965,366
[45] Date of Patent: Oct. 12, 1999

[54] METHODS OF IDENTIFYING PATIENTS HAVING AN ALTERED IMMUNE STATUS

[75] Inventors: Augusto C. Ochoa, Frederick; Howard A. Young, Gaithersburg; Dan L. Longo, Kensington; Paritosh Ghosh, Frederick, all of Md.

[73] Assignees: The United States of America as represented by the Secretary, Department of Health and Human Services, Washington, D.C.; Biormia USA Inc., Cranbury, N.J.

[21] Appl. No.: 08/880,671

[22] Filed: Jun. 23, 1997

Related U.S. Application Data

[62] Division of application No. 08/277,299, Jul. 22, 1994, Pat. No. 5,658,744.

[51] Int. Cl.$^6$ ........................................... C12Q 1/68
[52] U.S. Cl. ..................... 435/6; 435/29; 435/30
[58] Field of Search ..................... 435/6, 29, 30

[56] References Cited

U.S. PATENT DOCUMENTS

| | | | |
|---|---|---|---|
| 5,128,270 | 7/1992 | Delacroix et al. | 436/518 |
| 5,246,831 | 9/1993 | Skaletsky et al. | 435/5 |
| 5,260,186 | 11/1993 | Cercek et al. | 435/2 |
| 5,296,353 | 3/1994 | Ochoa et al. | 453/7.23 |
| 5,426,029 | 6/1995 | Rittershaus et al. | 435/7.21 |
| 5,556,763 | 9/1996 | Ochoa et al. | 435/7.23 |

OTHER PUBLICATIONS

P. A. Baeuerle, "The Inducible Transcription Activator NF—$_k$ B: Regulation by Distinct Protein Subunits", Biochimica et Biophysica Acta., 1072, (1991), pp. 63–80.
Farrar et al., "5–Azacytidine Treatment of a Murine Cytotoxic T Cell Line Alters Interferon–γ Gene Induction by Interleukin 2", J. of Immunology, vol. 135, No. 3, Sep. 1985, pp. 1551–1554.
Gray et al., "Structure of the Human Immune Interfone Gene", Dept. of Molecular Bio., vol. 298, No. 26, Aug. 1992, pp. 859–863.
Hardy et al., "Regulation of Expression of the Human Interfoneγ Gene", Proc. Natl. Acad. Sci., vol. 82, Dec. 1985, pp. 8173–8177.
Hu–Li et al., "Derivation of a T Cell Line That is Highly Responsive to IL–4 and IL–2 (CT.4R) and of an IL–2 Hyporesponsive Mutant of That Line", J. of Immunology, vol. 42, No. 3, Feb. 1989.
Kaye et al., "Both a Monoclonal Antibody and Antisera Specific for Determinants Unique to Individual Cloned Helper T Cell Lines Can Substitute for Antigen and Antigen–Presenting Cells in the Activation of T Cells*", J.Exp. Med., vol. 158, Sep. 1983, pp. 836–856.
Lederer et al., "Regulation of Cytokine Gene Expression in T Helper Cell Subsets", J. of Immunology, 1994, pp. 77–86.
Mizoguchi et al., "Alterations in Signal Transduction Molecules in T Lymphocytes from Tumor–Bearing Mice", Science, vol. 258, Dec. 1992, pp. 1795–1798.
Munoz et al., "Control of Lymphokine Expression in T Helper 2 Cells", Proc. Natl. Acad. Sci., vol. 86, Dec. 1989, pp. 9461–9464.
Norihisa et al., "Increased Proliferation, Cytotoxicity, and Gene Expression after Stimulation of Human Peripheral blood T Lymphocytes through a Surface Ganglioside (GD3)$^{1}$", J. of Immun., Oct., pp. 487–495.
Novak et al., cAMP Inhibits Induction of Interleukin 2 But Not of Interleukin 4 in T Cells, Proc. Natl. Acad. Sci., vol. 87, Dec. 1990, pp. 9353–9357.
Pang et al., "Interferon γ2, Protein Kinase C Activators, and Possible Effect of Hypomethylation on Gene Regulation", vol. 80, No. 3, Aug. 1992, pp. 724–732.
Weiss et al., "Role T3 Surface Molecules in Human T–cell Activation: T3–dependent Activation Results in an Increase in cytoplasmic free calcium", Proc. Natl. Acad. Sci., Vol. 81, Jul. pp. 4169–4173.
Samelson et al., "Association of the Fyn Protein–Tyrosine Kinase with the T–Cell Antigen Receptor", Proc. Natl. Acad. Sci., vol. 87, Jun. 1990, pp. 4358–4362.
Samelson et al., "Antigen Activation of Murine T Cells Induces Tyrosine Phosphorylation of a Polypeptide Associated with the T Cell Antigen Receptor", vol. 46, 1986, pp. 1083–1090.
Patel et al., "Multiple Kinases and Signal Transduction", J. of Bio. Chem., vol. 262, No. 12, Apr. 1987, pp. 5831–5838.
Lewis et al., "Restricted Production of Interleukin 4 by Activated Human T Cells", Proc. Natl. Acad. Sci., vol. 85, pp. 9743–9747.
Richard D. Klausner, "Architectural Editing: Determinating the Fate of Newly Synthesized Membrane Proteins", The New Bio., vol. 1, Oct. 1989, pp. 3–8.

(List continued on next page.)

*Primary Examiner*—David Saunders
*Attorney, Agent, or Firm*—Foley & Lardner

[57] ABSTRACT

Methods of identifying a patient having an altered immune status involve determining an immune status index for the patient and comparing it to the immune status index in healthy individuals. In general, an immune status index is the ratio of the amount of a protein that varies significantly in a patient with an altered immune status to the amount of another protein that is substantially invariant in both healthy and immune-altered individuals. Variable proteins can be TCR subunit proteins, T lymphocyte signal transduction pathway proteins, polynucleotide binding proteins or biological response modifiers (BRM). In addition, the ratio of a TH-1-type BRM to a TH-2-type BRM, the ratio of cytoplasmic to nuclear levels of polynucleotide binding proteins, the pattern of protein binding to an oligonucleotide probe that comprises the protein binding region of a gene for a BRM, or the pattern of distribution of T lymphocytes in a density gradient following density gradient centrifugation are also suitable as an immune status index. The methods are useful in identifying patients exhibiting immunosuppression, hyperimmunity and autoimmunity, as well as in assessing the immune status of a patient undergoing organ transplant.

10 Claims, No Drawings

OTHER PUBLICATIONS

Klausner et al., "T Cell Antigen Receptor Activation Pathways: The Tyrosine Kinase Connection", vol. 64, Mar. 1991, pp. 875–878.

Koning et al., "The Implications of Subunit Interactions for the Structure of the T Cell Receptor–CD–3 Complex", Eur.J. Immun., vol. 20, 1990, pp. 299–305.

Klausner et al., "The T Cell Antigen Receptor: Insights into Organelle Biology[1]", Annu. Rev. Cell Bio., vol. 6, 1990, pp. 403–431.

June et al., "Increases in Tyrosine Phosporylation are Detectable before Phospholipase C Activation after T Cell Receptor Stimulation[1]", J. of Immun., vol. 144, No. 5, Mar. 1990, pp. 1591–1599.

Imoden et al., "Transmembrane Signaling by the T Cell Antigen Receptor", J. Exp. Med., vol. 161, Mar. 1985, pp. 446–456.

Hsi et al., "T Cell Activation Induces Rapid Tyrosine Phosphorylation of a Limited Number of Cellular Substrates*", J. of Bio. Chem., vol. 264, No. 18, Jun. 1989, pp. 10836–10842.

Blumberg et al., "Structure of the T Cell Antigen Receptor: Evidence for Two CD3ε", Proc. Natl. Acad. Sci., vol. 87, Sep. 1990, pp. 7220–7224.

Berridge et al., "Inosital Phosphates and Cell Signaling ", Nature, vol. 341, Sep. 1989, pp. 197–205.

P. Ghosh et al., "Alterations in $NF_kB$/Rel Family Proteins in Splenic T–Cells from Tumor–bearing Mice and Reversal following Therapy", *Cancer Research* 54: 2969–2972 (1994).

P. Scott, "IL–12: Initiation Cytokine for Cell–Mediated Immunity", *Science* 260: 496–497 (1993).

METHODS OF IDENTIFYING PATIENTS HAVING AN ALTERED IMMUNE STATUS

This application is a continuation, division, of application Ser. No. 08/277,299, filed Jul. 22, 1994 now U.S. Pat. No. 5,658,744.

BACKGROUND OF THE INVENTION

The present invention relates to methods of identifying a patient who has an altered immune status compared to a normal status. The methods involve determining an immune status index for the patient and comparing the value of the index to the immune status index in healthy individuals. A significant variation between the patient's immune status index and the immune status index for healthy individuals indicates that the patient's immune status is altered. The present invention is used to identify patients with immunosuppression, hypersensitivity or autoimmunity as well as to monitor the immune response in general to facilitate medical treatment. The immune status index is used to stage or evaluate the progress of cancer therapy including chemotherapy, immunotherapy or surgery. The immune status index is used to evaluate a patient undergoing organ transplant and to evaluate the effect of ongoing therapy for autoimmune diseases or allergies.

The immune system is comprised of a complex array of precisely regulated cell types and the soluble molecules which these cells secrete. The immune response in a healthy individual involves recognition of a pathogen, other foreign material, or tumor cell followed by the elimination of the pathogen or other foreign material from the organism. Broadly speaking, the immune response can be divided into two categories, the innate responses and the adoptive responses. As a result of interactions among the components of the immune system, however, most immune responses comprise a variety of innate and adoptive mechanisms.

The innate responses are generally mediated by an important group of leukocytes known as phagocytic cells which include monocytes, macrophages and polymorphonuclear neutrophils. In general, these cell types act as a first line of defense against infection because they utilize non-specific recognition systems to bind microorganisms, internalize them and destroy them.

Central to the adoptive responses of the immune system are the lymphocytes. Lymphocytes specifically recognize individual pathogens whether they are inside host cells or outside cells in blood or in tissue fluids. Lymphocytes are generally divided into two groups, T lymphocytes (also called T cells) and B lymphocytes (also called B cells). The B cells release specific antibodies that combat extracellular pathogens and their products by binding to specific target molecules. T cells, on the other hand, have a wider array of responsibilities. Certain T cells interact with phagocytic cells to help the phagocytes destroy pathogens they have taken up. Other T cells recognize aberrant cells or cells infected by virus and destroy them. Still other T cells control B cell development and antibody production.

A definitive T cell marker is the T cell antigen receptor designated TCR. Among T cells in the blood, generally more than 95% of them are classified as TCR-2 and the remainder are TCR-1. TCR-1 and TCR-2 are distinguished on the basis of Ti subunits. The Ti subunits of the TCR-2 are two disulfide-linked polypeptides known as $\alpha$ and $\beta$. TCR-1 is structurally similar to TCR-2, but the TCR-1 Ti subunits are the $\gamma$ and $\delta$ polypeptides. Both TCR-1 and TCR-2 are associated with a complex of polypeptides which comprise the CD3 complex.

The TCR found on the surface of all T cells is composed of at least six different subunits which can be divided into three distinct subgroups of proteins. Klausner (1990). The heterodimers $\alpha\beta$ or $\gamma\delta$ within the receptor complex are responsible for ligand binding. Another subgroup of proteins which comprise the TCR are the CD3 chains which encompass at least four distinct, but closely related subunits. These subunits are $\gamma$, $\delta$, $\epsilon$ and $\zeta$. Koning (1990); Blumberg (1990). Diversification of receptor types is the result of segregation of chains of the TCR complex into multiple subunits. Incompletely assembled complexes are degraded, resulting in the surface expression of only completely assembled receptors. Klausner (1989).

T cells that are TCR-2 are subdivided into a subset of cells which carry the CD4 marker and another which carries the CD8 marker. The $CD4^+$ subset (TH) mainly induces immune responses while the $CD8^+$ subset (Tc) is largely composed of cytotoxic/suppressor cells. The $CD4^+$ subset is subdivided into those cells which positively influence the response of T cells and B cells. Another $CD4^+$ subset of cells induces the suppressor/cytotoxic functions of $CD8^+$ cells.

The $CD4^+$ subset is further subdivided into TH-1 and TH-2 type cells. TH-1 and TH-2 type cells are distinguished on the basis of the spectrum of lymphokines they secrete. TH-1 cells have been found to secrete interleukin-2 (IL-2) and IFN-$\gamma$, while TH-2 cells have been found to secrete IL-4, IL-5, IL-6 and IL-10. TH-1 and TH-2 cell types are thought to be derived from a common precursor population termed a TH-0 cell. In contrast to the mutually exclusive cytokine production of all or most of TH-1 and TH-2 cells, TH-0 cells produce all or most of these lymphokines. Treatment of TH-0 cells with IL-12 results in the production of TH-1-type cells. IL-12 is produced by macrophages and B cells.

TH cells appear to control and modulate the development of immune responses. TH cells play a major role in determining which epitopes become targets of the immune response and selection of effector mechanisms. The antigen-presenting cells (APCs) present processed antigen-to TH cells which recognize certain epitopes and thus select those which act as targets for the relevant effector functions. The TH cells then select and activate the appropriate effector cells including B cells that produce antibody and modulate the actions of other effector cells, Tc cells, natural killer (NK) cells, macrophages, granulocytes and antibody dependent cytotoxic (K) cells.

The release of different cytokines by TH cells may play a role in selection of effector mechanisms and cytotoxic cells. TH-1 cells secrete IL-2 and IFN-$\gamma$ which tend to activate macrophages and cytotoxic cells. In contrast, TH-2 cells secrete IL-4, IL-5, IL-6 and IL-10 and tend to increase production of eosinophils and mast cells as well as enhance production of antibody including IgE and decrease the function of cytotoxic cells. Once established, the TH-1 or TH-2 pattern is maintained through production of a cytokine that inhibits production of the other subset. The IFN-$\gamma$ produced by TH-1 cells inhibits production of TH-2 type cytokines such as IL-4, IL-10 while the IL-10 produced by TH-2 inhibits production of TH-1 type cytokines such as IL-2 and $\gamma$IFN.

In addition to determining which epitopes are to be the targets of the immune system, the immune system must also select the appropriate effector mechanisms for each infection. Effector mechanisms which can be selected include 1) cytotoxic T cell, 2) antibody plus mast cells and eosinophils or 3) macrophage activation and delayed hypersensitivity. Activation of inappropriate effector mechanisms can lead to enhanced susceptibility rather than protection.

The molecular mechanism by which T cell clones become restricted to express only certain lymphokine genes has remained obscure, although it has been reported that cAMP, or a labile regulatory protein, can inhibit expression of IL-2 in TH-2 cells. Novak (1990), Munoz (1989). Human B cell lines are capable of producing endogenous γIFN and this gene expression correlates, at least in part, with the methylation status of a SnaB 1 restriction enzyme site (TACGTA) present between the CAAAT and TATA box in the human γIFN promoter. Pang (1992). The SnaB 1 enzyme is methylation sensitive as it does not cleave DNA if the C is methylated at the 5 position, but does cleave DNA if the C is not methylated. Yang (1990). In a human B-cell line that expresses γIFN spontaneously, and in a murine T-cell line stably transfected with the human γIFN genomic DNA, this site was totally hypomethylated and completely cleaved by SnaB 1. Pang (1992).

Tc cells, also known as killer T cells, are effector cells which play an important role in immune reactions against intracellular parasites and viruses by lysing infected target cells. Cytotoxic T cells have also been implicated in protecting the body from developing cancers through an immune surveillance mechanism. Under certain conditions, $CD8^+$ T cells have also been shown to function as cells able to suppress the immunologic activity. This is mediated by the production of the raw factors produced by the TH-2 cells; i.e. IL4, IL10. T suppressor cells block the induction and/or activity of T helper cells. T cells do not generally recognize free antigen, but recognize it on the surface of other cells. These other cells may be specialized antigen-presenting cells capable of stimulating T cell division or may be virally-infected cells within the body that become targets for cytotoxic T cells.

Tc/Ts cells usually recognize antigen in association with class I Major Histocompatibility Complex (MHC) products which are expressed on all nucleated cells. Helper T cells, and most T cells which proliferate in response to antigen in vitro, recognize antigen in association with class II MHC products. Class II products are expressed mostly on antigen-presenting cells and on some lymphocytes.

In summary, the process of activation of the humoral (antibody and complement) or the cellular arm of the immune response and the regulation of such response appear to be controlled by the production of cytokines by T-cells and monocytes. Thus, it is likely that alterations in this regulation could result in the abnormal function of the immune response. This abnormal function could either be a decreased immune response resulting in immunosuppression, or alternatively in an abnormally increased response against one's own normal tissues in what is known as autoimmunity.

Determining the status of the immune response has mainly been done by clinical means. An "opportunistic infection," that is, the presence of an infection by a microorganism that normally is not pathogenic, suggests an immunosuppressed state. Alternatively, the presence of rheumatoid arthritis suggests an autoimmune process. Once the clinical findings occur, specific laboratory tests can confirm these findings. These laboratory tests mainly confirm that an altered immune system exists, for example, the antinuclear antibody test demonstrates the presence of autoantibodies in the serum of lupus patients, or the isolation of an opportunistic microorganism confirms the presence of an immunosuppressive process. However, there are no adequate tests to monitor the function of the immune system. Present immune tests on immune function include:

(1) Cell number: White blood cell count, $CD4^+/CD8^+$ ratio.
(2) Cell response: Proliferation index to tetanus toxoid.
(3) Antibody levels in serum.
(4) Lymphokine production: Tests absolute levels of lymphokines in serum.

None of these tests take into account the fact that the immune response is a balance between TH-1 and TH-2 responses. Considering the complex number of different specialized cell types that comprise the immune system, as well as the subtle control networks that exist among these cell types, it is not surprising that even small perturbations in this system can lead to serious illness in the patient. Many diseases are characterized by the development of an impaired or altered immune response. Progressive immunosuppression has been observed in patients with acquired immunodeficiency syndrome (AIDS), sepsis, leprosy, cytomegalovirus infections, malaria, cancer and the like. The mechanisms responsible for the down-regulation of the immune response, however, remain to be elucidated.

Deficits in T cell function have been proposed to play an important role in the immune impairment seen in cancer patients and tumor-bearing mice. Mizoguchi (1992) describe alterations in the signal transduction molecules in T cells from MCA-38 tumor-bearing mice that indicate these changes represent the molecular basis for functional impairments observed in splenic T cells isolated from these animals.

An imbalance in the immune system is evident in autoimmunity which is characterized by the production of autoantibodies and autoreactive T cells. The auto-immune disease may be organ-specific in the case of thyrotoxicosis or pernicious anaemia, or non-organ-specific in the case of scleroderma, systemic lupus erythematosus or rheumatoid arthritis. Other diseases which result from the establishment of an autoimmune response include lupus and autoimmune thyroiditis.

On the other hand, hypersensitivity occurs when an immune response occurs in an exaggerated or inappropriate form causing tissue damage. Hypersensitivity reactions are no more than a beneficial immune response acting inappropriately, thereby leading to inflammation and tissue damage. Certain types of hypersensitivity reactions are antibody-mediated while others are mediated primarily by T cells and macrophages.

In Type I hypersensitivity an IgE response is directed against innocuous environmental antigens such as pollen or animal dander. The acute inflammatory reaction with symptoms such as asthma or rhinitis is caused by the release of pharmacological mediators by IgE-sensitized mast cells. Antibody-dependent cytotoxic hypersensitivity or Type II hypersensitivity occurs when antibody binds to either self antigen or foreign antigen on cells. Type III hypersensitivity occurs when immune complexes are formed in large quantities or cannot be cleared adequately by the reticuloendothelial system. Type IV hypersensitivity is most seriously manifested when antigens are trapped in a macrophage and cannot be cleared. T cells are then stimulated to elaborate lymphokines which mediate a range of inflammatory responses.

T cell recognition events apparently lead to signal transduction and appropriate biochemical signals that control cellular responses. The ability of TCR to transduce signals to multiple biochemical cascades is a central event of immune cell activation. The details of this signal transduction pathway, however, are poorly understood. One or more tyrosine (Tyr) kinases likely have an essential role in T cell activation. Klausner (1991). At least two signal transduction pathways are activated upon stimulation of TCR by an antigen or by monoclonal antibodies directed against either CD3 or the αβ heterodimer.

Stimulation of TCR activates a tyrosine kinase. Samelson (1986); Patel (1987); Hsi (1989). Phosphorylation of several proteins with tyrosine residues is induced within seconds of TCR stimulation. June (1990). None of the TCR chains possesses intrinsic kinase activity. A member of the Src family of tyrosine kinases designated Fyn, however, coprecipitates with the CD3 complex. Samelson (1990). A T cell specific member of the Src family of tyrosine kinases, Lck, is tightly, but non-covalently, associated with the cytoplasmic domain of either a CD4 or CD8 molecule. The extracellular domains of CD4 and CD8 bind to MHC class II and class I molecules, respectively. Upon binding of TCR to an antigen-MHC complex on a presenting cell, the TCR is believed to be brought into close proximity with either a CD4 or CD8 molecule that is capable of independently binding to an appropriate MHC molecule.

TCR also activates a phosphatidylinositol-specific phospholipase C which leads to hydrolysis of phosphatidylinositol-4,5-bis-phosphate. Weiss (1984); Imboden (1985). This leads to the liberation of two second messengers: 1) inositol-1,4,5-tris-phosphate which is responsible for transient $Ca^{2+}$ mobilization; and 2) diacylglycerol which is a potent activator of protein kinase. Berridge (1989).

Another set of proteins that is related to signal transduction is the NF-κB/rel transcription factors, also known as the Rel-related protein family. Members of the Rel-related protein family all have similar primary amino acid sequences and bind to an array of homologous decanucleotide sequences with varying affinities. The NF-κB transcription activator is a multiprotein complex. The NF-κB transcription activator appears to be specialized in the organism to rapidly induce the synthesis of defense and signalling proteins upon exposure of cells to a wide variety of agents including cytokines, double-stranded RNA, T cell mitogens, DNA damaging agents, protein synthesis inhibitors, parasites, viruses and viral transactivators. A common denominator of the agents that activate NF-κB is that they either signal or represent a threat to cells and the organisms.

NF-κB is particularly suited to rapidly activate gene expression because (1) it does not require new protein synthesis, (ii) a simple dissociation reaction triggers activation, (iii) NF-κB actively participates in cytoplasmic-nuclear signalling and (iv) it is a potent transactivator.

NF-κB is involved in the inducible expression of the T cell growth factor IL-2, as well as the inducible expression of a component of IL-2 high affinity receptor, suggesting that NF-κB is a growth regulator. There is indeed a good correlation between the proliferative state of T cells and the state of NF-κB activity.

Three protein subunits, $I_\kappa B$, p50 and p65 control the biological functions of NF-κB. Members of the $I_\kappa B$ protein family display multiple homologous amino acid stretches (ankyrin repeats) that specifically interact with NF-κB/Rel proteins. IA includes a 35–43 kDa subunit which inhibits the DNA-binding of NF-κB and serves to retain NF-κB in an inducible form in the cytoplasm of unstimulated cells. Upon stimulation of cells, $I_\kappa B$ dissociates from the inactive complex with p65 and p50. The released p50–p65 complex heterodimer then migrates into the nucleus and transactivates genes. Constitutive expression of the IL-2 receptor α gene in hybrids between a T-cell and myeloma cell line depends solely on the presence of the heterodimer. Only p65 appears to bind $I_\kappa B$. Within cells, $I_\kappa B$ is released by modification of either $I_\kappa B$, p65 or both.

Rel proteins are capable of recognizing κB motifs. The $I_\kappa B$-family and Rel-family therefore comprise related proteins which are known to be involved in cytoplasmic/nuclear signalling. Other information on the NF-κB transcription activator and its relationship to the rel proteins may be found in Baeuerle (1991).

The present invention addresses limitations in the art for detecting and monitoring the immune status of a mammal as well as identifying appropriate treatment modalities. The present invention provides improved methods for evaluating the status of a patient's immune system. More specifically, the present invention provides improved methods for identifying, monitoring and evaluating the degree of immunosuppression, hyperimmunity or autoimmunity in a patient.

A need exists for effective methods of measuring the progression of immunosuppression so that attempts at augmenting the immune system in an immunosuppressed patient can be effectively timed. A need also exists for a method by which a patient's level of immunosuppression is estimated and used to accurately predict the likelihood of a patient's response to therapy. A need exists for a method to determine how much to suppress the immune response of a patient with autoimmunity. The patient's therapy can then be developed in a systematic fashion. A method is needed by which a clinician can determine whether a patient's T lymphocytes will be capable of activation and, thus, whether autologous adoptive immunotherapy will likely be efficacious. A need also continues to exist for a method of screening for immunosuppressive agents and agents that reverse or inhibit immunosuppression.

There is a need to detect tumors, in particular early in the development of a tumor, so that treatment effectiveness is enhanced. Also, improved methods for staging of cancer would facilitate choice of the most appropriate treatment modalities. There is also a need to test the effectiveness of treatment modalities prior to clinical trials, and as adjuncts to clinical trials.

There is a need for methods for detecting and measuring the degree of hyperimmunity or autoimmunity in the patient. In addition, improved methods for staging of the progression of hyperimmunity or autoimmunity would facilitate choice of the most appropriate treatment modalities as well as monitor the effectiveness of treatment modalities.

There is a need for methods of monitoring and evaluating the immune status of the patient receiving bone marrow or tissue transplants. Methods for monitoring and evaluating the immune status of the graft recipient, prior to the procedure, as well as after receipt of foreign tissue, are needed to effectively determine when immunosuppressive drugs should be administered.

The present invention addresses limitations in the art for evaluating, monitoring and predicting the status of a patient's immune system thereby providing a means to more effectively diagnose and treat patients with an altered immune status.

SUMMARY OF THE INVENTION

The present invention relates to methods of identifying and monitoring a patient having an altered immune status. The methods involve determining an immune status index for the patient and comparing it to the immune status index in healthy (control) individuals. A significant variation between the patient's immune status index and the immune status index for healthy (control) individuals indicates that the patient's immune status is altered. A "healthy patient" is defined herein as one not known to have a disease or condition associated with an altered immune state. The immune status index is used to identify patients with immunosuppression, hyperimmunity, or autoimmunity. The immune status index is used to stage or evaluate the progress of cancer therapy including chemotherapy, immunotherapy or surgery. The immune status index is used to evaluate a patient undergoing organ transplant.

In general, an immune status index is the ratio of the amount of a TCR subunit protein, a T lymphocyte signal transduction pathway protein, a polynucleotide binding protein, or a BRM that varies significantly in a patient with an altered immune status to the amount of another protein that is substantially invariant in healthy and immune-altered individuals. Alternatively, the ratio of a TH-1-type BRM to a TH-2-type BRM, the ratio of cytoplasmic to nuclear levels of certain polynucleotide binding proteins, the pattern of protein binding to an oligonucleotide probe that comprises the protein binding region of a gene for a BRM, methylation status of nucleotides within the regulatory element of a BRM gene, and the pattern of distribution of T lymphocytes in a density gradient following centrifugation of a lymphocyte preparation, is the immune status index. The methods are useful for identification of patients exhibiting immunosuppression, hyperimmunity and autoimmunity as well as assessing the immune status of a patients undergoing bone marrow, tissue, or organ transplants. The methods are useful for identifying compounds capable of altering the immune status of the patient, that is identification of compounds capable of inducing or reversing immunosuppression.

A distribution of each ratio in a sample of control patients and of patients known to have a condition predisposing to an altered immune state is developed. Threshold values to separate a "normal" from an "altered" immune state are determined depending on the sensitivity-specificity desired for a particular assay.

A fundamental concept of the present invention is that there is a balanced ratio of functions relating to the immune system maintained in a normal individual, and that the ratio is altered in diseases or malfunctions of the immune system. For example, during tumor growth, a myriad of alterations may occur, depending on the nature and extent of the tumor, and how long it has been in the host. The most informative way of understanding and staging the state of immune responsiveness and the effect of tumor progression on the immune response is evaluating the ratios of different markers, for example, TH-1 lymphokines/TH-2 lymphokines; (IL-2/IL-4; γIFN/IL-4; or IL-2/IL-10 and the like), CD3ζ chain/CD3ε chain, and/or cytoplasmic NF-κB/nuclear NF-κB. One ratio or a combination of ratios may be determined depending on which ratios are discriminatory of a particular disease or condition of interest.

In addition, the pattern of protein binding to an oligonucleotide probe that comprises the protein binding region of a biological response modifier (BRM) gene, such as the γIFN gene, is suitable to distinguish a TH-1 from a TH-2 immune response because the pattern of protein binding is different in the two cell types. Thus, these patterns of protein binding are a way of determining whether an individual's response is in a TH-1 or a TH-2 mode.

Alternatively, the methylation status of nucleotides within the regulatory element of a BRM gene, such as the γIFN, is suitable to distinguish a TH-1 from a TH-2 immune response because the pattern of DNA methylation is different in the two cell types. Determination of the methylation status within the regulatory element of a BRM gene allows one to assess whether an individual's immune response is in a TH-1 or a TH-2 mode. In addition, the pattern of distribution of T lymphocytes in a density gradient following centrifugation of peripheral blood cells can also be used as an immune status index.

As used herein, altered immune status refers to a deviation as defined by a threshold or the distribution of control values. Deviation may be caused by immunosuppression, autoimmunity or hyperimmunity or any other disease characterized by the malfunctioning of the immune system. An altered immune status is evaluated by determining an immune status index for the patient and comparing it to the immune status index in healthy individuals. A significant variation between the patient's immune status index and the immune status index for healthy individuals indicates that the patient's immune status is altered.

Substantially or significantly altered refers to a value outside of the statistical limits of the control distribution.

Abnormally high or low refers to a value of a ratio outside of the statistical limits of the control distribution.

As used herein, T lymphocytes or T cells include all subsets of lymphocytes which carry the T cell antigen receptor. These subsets include, e.g., lymphocytes which are $CD3^+CD4^+(\alpha\beta^+)$; $CD3^+CD8^+(\alpha\beta^+)$; $CD3^+CD4^-CD8^-(\gamma\delta^+)$; and $CD3^+CD56^+$.

As used herein, immunotherapy includes adoptive immunotherapy which includes cellular adoptive immunotherapy which involves the administration of immunologically active (immunocompetent) cells to an individual for the purpose of providing a beneficial immunological effect to the individual, such as reduction or control of cancerous or diseased tissue. Immunotherapy also includes cytokine therapy, vaccines, infusion of antibodies and chemo-immunotherapy.

As used herein, immunotherapeutic activity or immune response or immunologically active or immunocompetent includes anti-tumor activity, anti-infected cell activity, anti-disease agent activity and killer activity of white blood cells.

As used herein, the signal transduction pathway includes any protein, the expression of which is induced, linked or regulated by the binding of a ligand or an antibody to any T cell surface receptor. These proteins include, but are not limited to, Jun, Fos, Myc, GAP, Raf1, c-rel, Plcγ, Protein G, Inositol Phosphate, Protein Kinase C, Map1-kinase, CD45 phosphatase and the Src family of kinases including Lck, Fyn, Yes and Lyn. The signal transduction proteins also include DNA binding proteins, such as NF-κB, NFAT, etc.

As used herein, antibody includes any protein or protein analogue which binds specifically to an appropriate epitope of an antigen. Antibody includes any protein or protein analogue which binds specifically to an appropriate epitope of the T cell receptor that is stimulatory. Antibody also includes any protein or protein analogue which binds specifically to a TCR subunit protein, protein in the T lymphocyte signal transduction pathway, polynucleotide binding protein or BRM. The term includes antibodies made by conventional methods including polyclonals, monoclonals or fragments thereof, as well as genetically engineered or synthetic molecules, e.g., single chain antibodies, that contain a binding region that is the functional equivalent of an antibody in its binding specificity.

A diagnostically significant portion of a protein binding region of a BRM gene is defined as a region sufficient to distinguish a condition to be detected, from a control value.

As used herein, biological response modifier (BRM) includes those soluble proteins which mediate much of the intercellular signalling required for an integrated response to a variety of external stimuli. A BRM includes cytokines, which are potent mediators that interact with specific high affinity receptors on the cell surface. Cytokines have been shown to affect the function of all cell types involved in an immune response and to be involved in lymphopoiesis and hematopoiesis. They have been implicated in the patholarge number oa large number of diseases. Lymphokines are preferred cytokines in the claimed invention.

As used herein, the NF-κB/Rel family of transcription factors is a multiprotein complex which activates gene transcription. Several proteins including $I_\kappa B$, p105 (precursor of p50), p50 and p65 control the biological functions of NF-κB. NF-κB is a member of the Rel-related protein family which all have similar primary amino acid sequences and bind to an array of homologous decanucleotide sequences with varying affinities. Rel-related proteins can form a large number of distinct κB-binding dimeric complexes since most homo- and heterdimeric combinations are possible. The Rel protein family includes p50, p52, p65, v-Rel and c-Rel.

As used herein, polynucleotide binding protein is a protein or multiprotein complex that associates with DNA and thereby regulates transcriptional activity of a gene either by activating or repressing production of mRNA.

As used herein, oligonucleotide probe is a segment of nucleotides that hybridizes under stringent conditions to a sequence of nucleotides. As used herein a protein binding region of a gene or regulatory element of a gene is that region of DNA which binds a protein or multiprotein complex and thereby regulates transcriptional activity of a gene either by activating or repressing production of mRNA.

Further objects, features and advantages of the invention will become apparent form the detailed description of the invention which follows.

DETAILED DESCRIPTION

The process of alteration of the immune response in cancer involves changes in the structure of the TCR and alterations in the nuclear transcription factors such as NF-κB. All of these alterations support an interpretation that T helper cells in the presence of a tumor are shifting from a TH-1 response which drives a cellular response, to a TH-2 response which drives a humoral response.

It is possible that the immune response produced by the TH-0, TH-1 or TH-2 cells results in a diseased state that needs to be corrected. It is also possible, however, that the type of TH-0, TH-1 or TH-2 cells present in tumor bearing animals or cancer patients are not normal, especially given the major alterations seen in the TCR. Therefore these cells are designated herein as TH-2'.

Serum of mice with tumors exhibits increased levels of IL4 and IL10, as compared to a normal mouse, which indicates a TH-2 response. Moreover, a unique pattern of protein binding to an oligonucleotide probe that comprises the protein binding region of a gene for BRM occurs in TH-1 and TH-2 clones. For example, the binding pattern was determined using a 32 base pair probe from the promoter region of γIFN. This pattern was tested in the daughter T cells and the CD4$^+$ helper cells from normal mice, mice bearing tumor for 18 days and long-term tumor bearing mice (MCA-38 colon cancer). The pattern that appeared in the normal state matched that of the TH-1 clones. In contrast, the pattern of the tumor bearing mice, even though it did not match that of TH-2 cells, was nonetheless completely different from that of the normal TH-1-type pattern. TH-2 cells from tumor bearing mice (i.e. TH-2' cells) may be altered in more than one way.

The pattern of protein binding to DNA is useful to identify the shift from TH-1 to TH-2. Additionally, the concept of a TH-1→TH-2 shift opens up avenues to new therapeutic approaches which could reverse the process back to a TH-1 response. Thus, the ability of in vitro or in vivo manipulation or drugs to induce cells from long-term tumor bearers to revert back to a TH-1 pattern is used as a screen to select potential therapeutic agents. Likewise, a therapy (chemotherapy, radiation, surgery, immunotherapy or even gene therapy) can be monitored to determine if it is effective by demonstrating the ability of the therapy to shift the protein binding pattern of DNA in T lymphocytes to a TH-1 or a TH-2 response depending on the needed therapeutic outcome. These changes could occur even before a reduction in tumor is apparent. This assay is suitable to monitor the TH-1/TH-2 conversion, or to detect a TH-0 status in other diseases in which the immune response is important.

The process of loss of the cellular immune response with an increase in the antibody response in patients with advanced cancer was described in the 1960's. Based on current knowledge of immunology this alteration is explained by a change from a predominance of a TH-1 response (IL-2 and γIFN) to a TH-2 response (IL-4, IL-6, IL-10). In serum of tumor-bearing mice, there is an increase in the amount of IL-4 and IL-10 which is not detected in the serum of normal mice. Similarly, cultures of splenocytes from normal mice and mice bearing a tumor for short or long periods of time demonstrates that the first group produces mainly IL-2 and γIFN (TH-1). T cells from the tumor-bearing mice show a progressive loss of the ability to produce IL-2 and γIFN and instead produce IL-4.

A likely explanation for these observations is that a tumor produces a factor or a "signal" which induces major changes in the NF-κB molecules. In the tumor-bearing mouse model, the cytoplasmic p50, p65 and rel remain normal. However, the same factor which should be found in the nucleus is not seen and the p50 is replaced by a p48 form. It is possible that the translocation of these proteins to the nucleus is somehow blocked or that they are cleaved by a nuclear protease. In humans the major change is the loss of nuclear p65 and rel with decreased levels of nuclear p50. In general it is thought that the p65/p50 heterodimer is a stimulator of the production of IL-2, while the p50/p50 homodimer is a suppressor. If the p65 is not present in the nucleus as a result of degradation, blockage of translocation or lack of an appropriate translocation signal, then p50/p50 dimers would be preferentially formed. This would therefore be suppressive of the IL-2 gene and would decrease the production of IL-2. If the IL-2 (TH-1)- IL-4 (TH-2) production is normally balanced, the decrease in the production of IL-2 suggests that there is a relative increase of IL-4 activity, even though the absolute amount may not be altered, thus effectively driving the response into a TH-2 pattern.

One measure of the immune status index is the ratio of the amount of a TCR subunit protein or T lymphocyte signal transduction pathway protein that varies significantly in a patient with an altered immune status, to the amount of another protein that is substantially invariant in healthy and immune-altered individuals. In U.S. patent application Ser. Nos. 07/863,262, now U.S. Pat. No. 5,296,353, and 08/034, 832, now U.S. Pat. No. 5,556,763, the contents of said applications being incorporated herein by reference, it was disclosed that there is a marked decrease in the therapeutic efficacy of adoptively transferred T lymphocytes from murine hosts bearing MCA-38 tumor for >30 days (late tumor-bearing mice or late TBM) as compared to normal mice and mice bearing tumor for <21 days (early tumor-bearing mice or early TBM).

T lymphocytes from late TBM lose the expression of the CD3ζ and CD3γ chains into the TCR. The CD3ζ chain is in turn replaced in the TCR by the Fcεγ chain, a member of the ζ family of chains. These lymphocytes also exhibit a marked decrease in T lymphocyte signal transduction pathway proteins such as tyrosine kinases of the Src family, notably LcK and Fyn, as well as proteins PLCγ and GAP. On the other hand, integration of CD3ε into the TCR is substantially unchanged. Similar changes in the pattern of integration of proteins into the TCR and expression of proteins in the signal transduction pathway have been observed in human cancer patients.

The immune status index, therefore, is determined by immuno-precipitating the TCR complex from a known quantity of cells. The ratio of the amount of a TCR subunit protein integrated into the TCR complex that varies significantly in a patient with an altered immune status, such as CD3ζ, CD3γ or Fcεγ, to the amount of another TCR protein that is substantially invariant in healthy and immune-altered individuals, such as CD3ε, or TCRαβ, constitutes an immune status index.

In another illustrative embodiment, an immune status index constitutes the ratio of the amount of a T lymphocyte signal transduction pathway protein that varies significantly in a patient with an altered immune status, such as LcK, Fyn or PLCγ, to the amount of another protein that is substantially invariant in healthy and immune-altered individuals, such as CD3ε or TCRαβ.

Another immune status index is the ratio of the amount of a BRM that varies significantly in a patient with an altered immune status to the amount of another protein that is substantially invariant in healthy and immune-altered individuals. This type of immune status index is, e.g., the ratio of the amount of a TH-1-type BRM to a TH-2-type BRM. For example, an immune status index is the ratio of TH-1 lymphokines/TH-2 lymphokines. More specifically an immune status index is the ratio of IL-2/IL-4; γIFN/IL-4; or IL-2/IL-10, and the like.

Another immune status index is the ratio of the amount of cytoplasmic to nuclear levels of certain NF-κB/rel proteins, or the ratio of the amount of certain NF-κB/rel proteins that varies significantly in a patient with an altered immune status to the amount of another protein that is substantially invariant in healthy and immune-altered individuals. In U.S. patent application Ser. No. 08/034,832, now U.S. Pat. No. 5,556,763, the contents of said application being incorporated herein by reference, it was disclosed that in some abnormal conditions, c-Rel, p65 and p50 are absent. In other conditions, only one or two are absent, or the protein is absent from the nucleus but not the cytoplasm. In still other abnormal conditions, new forms of protein replace a form present in the normal state.

For example, in the presence of RENCA tumor and MCA-38 colon tumor in a mouse, the p50 protein, a component of nuclei of a T lymphocyte preparation from a non-tumor bearing mammal, disappears, and is replaced by p48 and p46 (proteins with estimated molecular weights of 48 and 46 kD respectively as determined by Western blots.) Some of the new protein forms appear to be related to the larger molecular weight form they replace by N-terminal truncation of the larger form. Analysis of the pattern of NF-κB/rel proteins in melanoma patients revealed alterations from the non-cancerous state. c-Rel and p-65 were absent in nuclear preparations.

Thus, an immune status index is the ratio of the amount of cytoplasmic to nuclear levels of p65 and c-Rel. For example, an ELISA method for the determination of the ratio of cytoplasmic to nuclear amounts of p65 and c-Rel comprises preparation of samples of tissue or fluid, such as blood, containing T lymphocytes. In the case of human T lymphocytes, the cells must be stimulated, such as by incubation for 1 or more hours with an anti-CD3 antibody, in order to detect p65 translocation to the nucleus. The cells in the T lymphocyte preparation are subsequently gently lysed so that nuclei remain intact. The intact nuclei are gently separated from the cytoplasmic components, e.g., by means of low speed centrifugation.

For example, the cell lysates containing intact nuclei are placed in microtitre plate wells and the plates are centrifuged at low speed to sediment the intact nuclei, for example at 2,000 rpm for 5 min. The supernatant containing the components of the cytoplasm are removed and placed in separate wells. The nuclei are lysed and the amount of p65 and c-Rel in each of the nuclear and cytoplasmic fractions is quantified. The immune status index is the ratio of the amount of cytoplasmic to nuclear p65 and c-rel.

Alternatively, an immune status index is the ratio of the amount of nuclear levels of p65 and c-Rel to the amount of another protein, e.g., nuclear MAP kinase that is substantially invariant in healthy and immune-altered individuals. The amounts of nuclear p65 and/or c-Rel, and MAP kinase are determined following purification of intact nuclei, and the immune status index is expressed as the ratio of the amount of nuclear p65 and c-Rel to the amount of the substantially invariant protein.

The amount of TCR subunit protein, T lymphocyte signal transduction pathway protein, NF-κB/rel protein, BRM, or polynucleotide binding protein can be determined by many different conventional and well known assay methods. Samples of tissue or fluid such as blood are isolated from the patient and the amount of the selected protein is determined. These samples are taken from various tissues including tumor tissue, splenic or lymphatic tissue, peripheral blood cells, cerebrospinal fluid, pleural effusions and ascites.

A protein extract of the tissue or cell sample is analyzed directly to determine the amount of the protein. Alternatively, T cells, T cell subsets, nuclear cell fractions or cytoplasmic cell fractions are purified before determining the amount of the selected protein. T cells or T cell subsets are purified by any of a variety of conventional techniques such as rosetting followed by Ficoll®-Hypaque® gradient centrifugation, indirect panning, antibody/complement-mediated cytotoxicity, immunomagnetic purification, flow cytometry, and similar techniques. Additionally, the TCR are immunoprecipitated using an antibody such as anti-CD3ε. The subunit proteins comprising the TCR are analyzed by Western blot by methods known to those of skill in the art.

The amount of a protein is determined using well known techniques such as immunofluorescence, ELISA, Western blot analysis, and similar techniques. An extract for analysis of protein by any of these well known techniques is made by conventional methods from the tissue or fluid sample, or T cells or T cell subsets prepared from these samples. An antibody which specifically detects the selected protein, and which is conjugated to a known label, is prepared by methods known to those of skill in the art.

A kit for determining the immune status of a patient includes an antibody directed to a protein from a group including a TCR subunit, a signal transduction pathway protein, a BRM, a polynucleotide binding protein and a NF-κB/rel family protein. In separate containers, one or more antibodies are present, each directed to an individual protein of the present invention. The kit also includes means for detecting the formation of an antigen-antibody complex, from which the presence of a particular protein is inferred and quantitated. Immune status indices, as described above, are calculated based upon the amount of each protein detected.

Immunoassay-based diagnostic kits of the present invention are typically used in an ELISA format to detect the presence or quantity of proteins in a sample such as a lymphocyte preparation. ELISA refers to an enzyme-linked immunosorbent assay that typically employs an antibody or antigen bound to a solid phase and an enzyme-antigen or enzyme-antibody conjugate to detect and quantify the amount of antigen present in a sample. A description of al. ELISA technique is found in Sites et al. (1982) and in U.S. Pat. Nos. 3,654,090, 3,850,752 and 4,016,043, each of which are incorporated herein by reference. Suitable reagents in the kits in separate containers include:

1. a. a kit for cell separation including a column to eliminate B cells, granulocytes and monocytes;
   b. a cell lysis kit containing the lysate reagents;
   c. ELISA plate with antibodies bound to it or individual vials of polyclonal anti-CD3 capture/murine monoclonal to CD3ζ, CD3γ, Fcεγ or CD3ε as a probe/ alkaline phosphatase-coupled goat anti-murine Ig.
2. a. a kit for cell separation including a column to eliminate B cells, granulocytes and monocytes;
   b. a cell lysis kit containing the lysate reagents;
   c. transfer of lysate to ELISA plate for separation of nuclear and cytoplasmic fractions by means of centrifugation;
   d. ELISA plate with antibodies bound to it or individual vials of murine monoclonal to p65 or c-Rel and a probe such as alkaline phosphatase-coupled goat anti-murine Ig, or any other equivalent probe well known to the skilled artisan.

Another type of immune status index can be obtained using the pattern of protein binding to an oligonucleotide probe that comprises the protein binding region of a BRM gene, such as the γIFN gene. The pattern of protein binding to the oligonucleotide probe that comprises the protein binding region of a BRM gene is determined by methods well known to the skilled artisan, such as the electrophoretic mobility shift assay (EMSA). Norihisa (1994). The oligonucleotide probe that comprises the protein binding region of a BRM gene can be a nucleotide sequence that does not include a κB sequence. An immune status index that is the pattern of protein binding to an oligonucleotide probe that comprises the protein binding regions of a BRM gene is suitable to distinguish a TH-1 from a TH-2 immune response, or to detect a TH-2' immune response, because the pattern of protein binding is different in these cell types. Thus, these patterns of protein binding are a way of determining whether an individual's response is in a TH-1, TH-2 or TH-2' mode.

An immune status index is the methylation status of nucleotides within the regulatory element of a BRM gene. The methylation status of nucleotides within the regulatory element of a BRM is determined by means of methods well known to the skilled artisan. For example, a restriction enzyme is selected that is sensitive to the methylation status of the restriction enzyme's target sequence. Depending upon whether the target sequence methylated or not, a particular restriction enzyme may or may not cleave the target and product(s) are detected by means of Southern blot analysis using a hybridization probe that comprises a nucleotide sequence that includes the target sequence of the restriction enzyme. The methylation status of nucleotides within the regulatory element of a BRM gene provides a way of determining whether an individual's response is in a TH-1 or a TH-2 mode.

More specifically, the methylation status of CpG dinucleotide contained within a TATA-proximal regulator element of the γIFN promoter correlates with the transcription of the γIFN gene. In murine TH-1 clones and two human CD4$^+$ clones which produce γIFN and IL-2, this site is either completely or partially hypomethylated. In contrast, in murine TH-2 clones which produce IL-4 and IL-5, but do not produce γIFN or IL-2, this site is greater than 98% methylated. Treatment of murine TH-2 cell lines with 5-azacytidine, an agent that inhibits methylation of the DNA, converts these cells to γIFN producers.

A remarkable and attractively simple type of immune status index can be derived from the pattern of distribution in a density gradient, of T lymphocytes obtained from a patient and subjected to density gradient centrifugation, compared to the pattern of distribution in a density gradient, of T lymphocytes obtained from a healthy individual and subjected to density gradient centrifugation. The pattern of distribution, in a density gradient of T lymphocytes obtained from an individual with an altered immune status significantly differs from the pattern of distribution, in a density gradient, of T lymphocytes obtained from a healthy individual.

Depending upon the nature of the altered immune status, the patient may have fewer, or alternatively, more T lymphocytes in one or more bands in the density gradient. The change in the pattern of distribution in the density gradient of T lymphocytes from the patient, compared to the healthy control, evidences a change in the size and physiology of the T lymphocytes and is diagnostic of a change in the patient's immune status. The change in the pattern of distribution of T lymphocytes in the density gradient is correlated with the type and severity of disease. The pattern of distribution of T lymphocytes in the density gradient also can be used to monitor recovery of the patient, i.e. restoration of a normal immune status. The pattern of distribution of T lymphocytes in the density gradient can be used to identify compounds that alter the immune status of the individual, such as compound that induce or reverse immunosuppression.

Any material that is gentle to cells, that is, which does not disrupt the cells or significantly change membrane permeability, can be used to produce the density gradient. For example, Percoll® (polyvinylpyrollidone), Ficoll® (sucrose polymer), Hypaques (3,5-Bis-acetamido-2,4,6-tri-iodobenzoic acid, sodium), sucrose, dextrans or other sugar polymers, are appropriate materials for production of the density gradient. The density gradient can be continuous or discontinuous. The range of densities in the gradient can be varied so long as the cells are separated in a diagnostically meanful manner.

Percoll® density gradient centrifugation of human peripheral blood lymphocytes revealed that size correlated with density. Most of the T lymphocytes from healthy individuals were found in most dense Fraction 6 while a small proportion of the T lymphocytes were found in the less dense Fraction 3. The cells in Fraction 6 are smaller than those in Fraction 3. In cancer patients, on the other hand, the majority of T lymphocytes were found in the larger and less dense Fraction 3. Accordingly, the cells may be separated on the basis of density or size, such as by fluorescence activated cell sorting (FACS).

The immune status index can be expressed as a change in the pattern of distribution of T lymphocytes in the density gradient. Alternatively, the immune status index can be expressed quantitatively as the ratio of the number of cells, or amount of protein, in specific density gradient fractions, so long as the cells isolated from patient and control are prepared by the same method and equal numbers of cells are applied to each gradient. In addition, the immune status index can be expressed as the relative amounts of a TCR subunit protein, a T lymphocyte signal transduction pathway protein, a polynucleotide binding protein, or a BRM in T lymphocytes from specific density gradient fractions. Alternatively, the immune status index is the ratio of a TH-1-type BRM to a TH-2-type BRM, the ratio of cytoplasmic to nuclear levels of certain polynucleotide binding proteins, the pattern of protein binding to an oligonucleotide probe that comprises the protein binding region of a gene for a BRM, and the methylation status of nucleotides within the regulatory element of a BRM gene in T lymphocytes from one or more density gradient fractions. A significant variation between the patient's immune status index and the immune status index for healthy (control) individuals indicates that the patient's immune status index is altered.

An illustrative kit containing the necessary materials for rapid and reproducible separation of T lymphocyte fractions by density gradient centrifugation under sterile conditions, and reagents for the determining the immune status of cells in the fractions is provided. A kit for determining the immune status index of a patient typically would include centrifugation tubes and materials for preparation of the density gradient, such as sterile solutions of Percoll®, describe generically of various densities. The kit can contain a cell lysis kit containing cell lysis reagents. Alternatively, the kit contains materials for cell separation such as a column to eliminate B cells, granulocytes or monocytes. The kit can contain pipettes for removal of cell fractions following density gradient centrifugation. The kit may contain reagents for the stimulation of separated T cell fractions, such as the anti-CD3 antibody and cell culture medium.

The kit also can contain reagents for determining the amount of one or more diagnostic proteins in a density gradient fraction. The kit can contain one or more ELISA plates with antibodies bound to it, or individual vials containing antibodies to p65, c-Rel, p50, or BRM such as IL-2, IL-4, etc. The kit can contain a probe such as alkaline phosphatase-coupled goat anti-murine Ig, or any other probe well known to the skilled artisan.

In place of, or in addition to, reagents for determining the amount of one or more diagnostic proteins in the density gradient fraction, the kit can contain reagents for determining the pattern of protein binding to an oligonucleotide probe that comprises the protein binding region of a BRM gene or the methylation status of nucleotides within the regulatory element of a BRM gene. These reagents include an oligonucleotide probe for use in EMSA analysis of nuclear extracts prepared from the cell fraction. Alternatively, the reagents can include one or more restriction enzymes and a DNA hybridization probe for determining the methylation status of nucleotides within the regulatory element of a BRM gene.

The T lymphocyte preparation is obtained from any source of T lymphocytes such as spleen, peripheral blood, tumor, lymph nodes, thymus, etc. For example, peripheral blood lymphocytes are obtained by conventional methods and red blood cells are removed by lysis. Intact live cells are separated from cell debris and dead cells by means of centrifugation. The T cells are then subjected to density gradient centrifugation, for example density gradient centrifugation in Percoll®, Ficoll® or sucrose. The pattern of distribution of T cells obtained from the T cell preparation from healthy controls and patients suspected of having an altered immune status are compared following density gradient centrifugation.

An immune status index also can be expressed as a ratio, or other relationship, of any one of the immune status indices, as determined by any of the methods outlined above, to an immune status index, as determined by any of the other methods outlined above. An immune status index also can be a combination of said individual ratios.

A significant variation between a patient's immune status index, as determined by any of the methods outlined above, and the immune status index in healthy individuals determined by the same method, indicates that the patient's immune status is altered. It is contemplated that an immune status index is used to detect and monitor immunosuppression, such as the immunosuppression commonly associated with cancer. An immune status index is used to determine the patient's therapeutic plan. For example, the physician determines an immune status index to evaluate the level of immunosuppression of the patient's own T lymphocytes and to determine the likelihood of success that these cells can be stimulated for effective autologous adoptive immunotherapy. U.S. patent application Ser. No. 07/910,835, now U.S. Pat. No. 5,316,763, discloses methods of adoptive immunotherapy. Likewise, the immune status index can be used to aid the physician in determining when to treat the immunosuppressed patient with immunostimulating drugs, antibacterial agents, and the like.

Diseases which result in progressive immunosuppression include cancer of many different tissues including leukemia, Hodgkin's disease, lung cancer, colon cancer, gliomas, renal cell carcinoma, and the like. Progressive immunosuppression is observed in a great variety of infections including those that are intracellular such as leprosy, tuberculosis, leishmania; those that are extracellular such as sepsis, kiseases of viral etiology such as those caused by HIV, cytomegalovirus, Epstein Barr, and the like; parasitic infections such as schistosomiasis, malaria, and the like.

If chemotherapy, radiotherapy, surgery, medication, immunotherapy or some other treatment modality, or combination of treatment modalities, is effective in eliminating the tumor, or other cause of immunosuppression, then the immune status index should return to normal. These improvements are monitored by the methods of the present invention.

It is contemplated that the immune status index is suitable to detect and monitor autoimmunity. For example, the immune status index is suitable to determine the patient's therapeutic plan. Diseases which result in the establishment of autoimmune response include lupus, autoimmune thyroiditis, scleroderma, rheumatoid diseases such as rheumatoid arthritis, and the like.

It is contemplated that the immune status index is suitable to detect and monitor hyperimmunity. For example, the immune status index is used to determine the patient's therapeutic plan.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Antibodies to the ζ Protein

Polyclonal and monoclonal antibodies were made to two different Keyhole Limpet Hemocyanin (KLH)-conjugated peptides having amino acid sequences based on the sequence of the human ζ protein. The antibodies were prepared by Multiple Peptide Systems, now Chiron Mimotopes Peptide Systems.

The amino acid sequence of peptide 1 was RRRGKGHDGLYQGC-NH2(SEQ ID NO:1). The antibodies made to peptide 1 were designated:

Polyclonal: AB70-92A
Monoclonal: MAB3-92A

The amino acid sequence of peptide 2 was DTYDALHMQTLAPRC-NH2(SEQ ID NO:2). The antibodies made to peptide 2 were designated:

Polyclonal: AB70-92B or Oncoζ1
Monoclonal: MAB12-92

The polyclonal antibodies were prepared by means of the following protocol. 5 mg of purified peptide was coupled through the terminal cystein thiol to KLH with the heterobifunctional cross-linking agent MBS (Maleimidobenzoyl-N-hydroxysuccinimide ester), in a ration of 1 part peptide to 1 part KLH (w/w). The host were New Zealand while rabbits 6–12 months in age. The peptide was suspended in PBS buffer (3.1 mg/ml), emulsified by mixing with an equal volume of Freund's Adjuvant and injected into five to six subcutaneous dorsal sites for a total volume of 0.6 ml (1.0 mg of conjugate, 0.50 mg peptide) per immunization.

Animals were bled from the ear vein and the blood was then heated at 37° C. for 1 hours, cilled at 0° C. for 15 hours nd centrifuged. The serum was stored at −20° C. The pre-immune bleed, first bleed, second bleed and third made were made on days 1, 46, 49 and 53, respectively. In order to control the effectiveness of the immunization, the pre-immune serum and the first bleed were tested by ELISA with KLH as coat. For all sera, the anti-peptide antibody titer was determined by means of ELISA with free peptide as coat (100 pmoles/well). Prior to use, the polyclonal antibodies were affinity purified on a column to which was attached the synthetic purified peptide using methods well known to the skilled artisan.

The monoclonal antibodies were prepared by as described in U.S. Pat. No. 5,246,831, which is incorporated herein by reference. The criteria used for selection of the anti-ζ monoclonal antibodies were as follows. In the first fusion, all hybridomas that produce detectable antibody to the antigen are selected. The peptides antigens were absorbed to microliter wells of ELISA plates for this testing purpose. All positive fusion cultures were expanded in volume and re-tested in the same manner. Approximately 5 of the cultures having the highest OD values according to ELISA were then selected for subcloning to ensure monoclonality. Resulting subclones were then tested in the same manner as in the initial screen to detect all positive subclones.

Once again, positive subclones were expanded, retested and the culture having the highest OD values according to ELISA were selected. Finally, the 5 expanded subcultures having the highest OD values were expanded for injection into mice for ascites production. Accordingly, it is well within the skill level of the artisan in this field, without undue experimentation, to prepare other monoclonal antibodies having the same antigen binding characteristics as MAB3-92A and MAB12-92.

EXAMPLE 2

ELISA Assay for CD3ε and ζ Proteins

The CD3ε chain contained in detergent lysates of peripheral blood cells (PBLS) or of human T cell lines was measured by a sandwich ELISA assay. Detergent lysates of cells were prepared by resuspending the cells at a concentration of 1×10⁶/10 μl of lysis buffer (50 mM Hepes pH 7.4, 150 mM NaCl, 1 mM sodium orthovanadate, 1 mM EDTA, 10 μg/ml leupeptin, 10 μg/ml aprotinin) containing either 0.5% triton X-100 (Sigma) or 1.0% digitonin (Wako BioProducts). After incubating 30 min on ice, the suspensions were centrifuged at 14,000 rpm for 5 min (Eppendorf Microcentrifuge Model 5415C).

The CD3ε complex was first captured on 96-well-plates (Nunc MaxiSorp) coated with an affinity-purified rabbit polyclonal anti-CD3κ antibody (DAKO, catalogue #A452). The antibody-bound complex was then detected using a murine monoclonal anti-CD3 antibody recognizing a separate epitope (Coulter, OKT3). Binding of the murine antibody was detected using an alkaline phosphatase-coupled goat anti-murine Ig reagent (Southern Biotech, catalogue #1010-04) followed by addition of the alkaline phosphatase substrate, p-nitrophenyl phosphate (pNPP, Sigma, catalogue #2765).

The 96-well plates were coated with primary antibody by incubating overnight at 4° C. with 100 μl/well of rabbit anti-CD3ε at 5 μg/ml in phosphate buffered saline (PBS). The antibody solution was removed by flicking the contents of the plate and the plates were subsequently incubated for 2 h at 4° C. with 200 μl/well of PBS containing 2% w/v dry nonfat milk to block absorption sites. Blocking solution was removed and the plates were washed 2× with 150 μl PBS/well.

Cell lysates were added to appropriate wells and incubated 1h at 4° C. The plates were washed 5× with 150 μl PBS, followed by addition of 100 μl/well of secondary murine anti-CD3 reagent (5 μg/ml in PBS containing 0.2% milk). Following a 30. min incubation at 4° C., the plates were again washed 5× with 150 μl PBS. Alkaline phosphatase-coupled goat anti-murine Ig reagent (100 μl/well of a 1:500 dilution in PBS containing 0.2% milk) was added and the plates were incubated another 30 min at 4° C. After washing 5×, nNPP substrate (100 μl of 1 mg/ml in 10% diethanolamine, 240 μM MgCl₂, pH 9.8) was added to each well. The plates were incubated at 37° C. for 30 to 60 min.

Absorption readings were made at 405 nm on a Bio-Tek Model EL 312e microplate spectrophotometer. Background controls were included in which primary antibody, lysate or secondary antibody were replaced with PBS in the protocol. Detergent lysates of B cell lines negative for CD3ε and ζ expression based on immunofluorescence were used as additional controls.

The ζ protein was measured using two different protocols. In Protocol 1, rabbit anti-CD3ε (DAKO #A452) was used on the plates to capture detergent-solubilized complexes containing CD3ε and ζ protein. The amount of antibody-bound ζ protein was then measured using a murine monoclonal anti-ζ reagent (Coulter TCR-ζ, catalogue #6604592) and alkaline phosphatase-coupled goat anti-murine Ig.

In Protocol 2, a murine monoclonal anti-ζ antibody (Coulter CD3ζ) was used to capture detergent-solubilized ζ protein directly, followed by detection of bound ζ using a rabbit polyclonal anti-ζ antibody and alkaline phosphatase-coupled goat anti-rabbit-polyclonal antibody (Southern Biotech, catalogue #4010-04). The rabbit polyclonal anti-ζ antibody was Oncor1 coupled to carrier protein KLH. The assays were performed as in the CD3ε assay above, using primary Ab at 5 μg/ml to coat the plates and secondary antibody at 5 μg/ml (Coulter TCR-ζ) or at a 1:300 dilution of crude sera.

Typical results using the CD3 ELISA assay and the two versions of the ζ ELISA assay are shown in Table 1. In all three assays, detergent lysates prepared from normal human peripheral blood T cells or T cell lines gave absorption values far above those obtained using lysates from ζ-negative B cell lines or from controls in which the primary Ab was excluded.

The digitonin lysis buffer was clearly superior to triton X-100 for measurement of CD3-ζ association using anti-CD3 as the capture reagent and anti-ζ for detection (ζ Protocol #1) while triton X-100 lysates appeared slightly superior for measuring ζ antigen using the combination of two anti-ζ Abs for capture and detection (ζ Protocol #2). Both digitonin and triton lysis buffers performed well in the CD3 assay. A likely explanation for the differences between the two ζ assay protocols is that digitonin may preserve the noncovalent association of ζ and CD3ε while triton X-100 may cause its dissociation. Another point to consider in using the two ζ assay protocols is that the anti-CD3ε /anti-ζ protocol focuses on the level of ζ chain associated with CD3 on the surface of CD3-positive T cells while the anti-ζ/anti-ζ protocol measures ζ content regardless of its association with CD3 or its location in T cells or other types of ζ-positive cells (i.e., natural killer cells). For the purposes of the immune status index it is necessary to measure the ζ actually incorporated into the CD3.

Also shown in Table 1 is the ratio of absorbance values in the ζ and CD3ε assays. Because the proportion of CD3-positive T cells in peripheral blood and the amount of CD3ε per cell may vary, the ratio offers a convenient way to normalize ζ levels to CD3 content without requiring purification of T cells from the samples.

TABLE 1

Capture ELISA Assays of Zeta and CD3*

| Cell Sample | ZETA Protocol 1 | ZETA Protocol 2 | CD3ε | Ratio** ζ/CD3ε |
|---|---|---|---|---|
| Normal T cells | | | | |
| Digitonin lysate | 0.517 | 0.701 | 0.806 | 0.87 |
| Triton lysate | 0.022 | 1.280 | 1.099 | 1.16 |
| Jurkat T cell line | | | | |
| Triton lysate | ND*** | 0.849 | 1.310 | 0.64 |
| B cell lines | | | | |
| RL | | | | |
| Digitonin lysate | 0.001 | 0.030 | 0.000 | — |
| Triton lysate | 0.035 | 0.047 | 0.000 | — |
| HT | | | | |
| Triton lysate | ND | 0.014 | 0.000 | — |
| No primary Ab Control | | | | |
| Normal T cells | | | | |
| Triton lysate | ND | 0.027 | 0.001 | — |
| Digitonin lysate | 0.012 | ND | 0.000 | — |

*Optical Density 405
**Ratio of absorbance values wherein ζ values used in determining the ratio of ζ to CD3ε were derived using Protocol #2
***ND = not done Application of the CD3ε and ζ capture ELISA assays to mixed cell populations containing significant proportions (10%) of polymorphonuclear cells (PMNs) requires special precautions due to the release of proteases from such cells during the detergent lysis step. In such instances, a modified lysis buffer is employed which contains additional protease inhibitors. Examples of such inhibitors include soybean trypsin/chymotrypsin inhibitor (200 μg/ml, Sigma), chymostatin 200 7 μg/ml, Boehringer Mannheim) and phenyl methyl sulphonyl fluoride (2 mM). As shown in Table 2, in mixed cell populations containing a high proportion of PMNs (RC-PBL sample), these three protease inhibitors cause a dramatic increase in the amount of measurable ζ chain, implying that ζ chain is particularly sensitive (relative to the CD3 chain) to proteolytic destruction. Purification of T lymphocytes from the mixed cell population (RC-T sample) has a comparable effect.

TABLE 2

Effect of Protease Inhibitors on the ζ/CD3 ELISA Assay

| Sample | Protease Inhibitors | % PMNs | Zeta Protocol 1 | CD3ε | Ratio γ/CD3ε |
|---|---|---|---|---|---|
| RC-PBL | − | 55 | 0.050 | 0.342 | 0.15 |
| | + | 55 | 0.229 | 0.354 | 0.65 |
| RC-T | − | 7 | 0.346 | 0.455 | 0.76 |
| | + | 7 | 0.610 | 0.504 | 1.21 |

*optical Density 405 nm.
**Ratio of absorbance values wherein ζ values used in determining the ratio of ζ to CD3ε were derived using Protocol #1

EXAMPLE 3

Cell-Based Immunoassay of CD3ε and ζ Proteins

In this protocol CD3ε and ζ proteins are measured with a 96 well microliter plate format employing intact fixed cells. Lymphocytes or other cells are fixed to the wells of the microliter plate using such reagents as paraformaldehyde, methanol, etc., followed by permeabilization with detergents (digitonin or triton X100, etc.). Primary antibodies to CD3ε, or other proteins of interest are added to the appropriate wells and their binding is detected using biotinylated secondary antibody reagents and avidin probes labeled with enzymes (alkaline phosphatase, etc.), fluorescent molecules (europium, etc.), or radioisotopes (125, etc.).

In the cell-based immunoassay 50 μl of T cells ($5 \times 10^4$) were added to each well and the liquid was allowed to evaporate. The cells were fixed and permeabilized simultaneously with a cold solution of 1% paraformaldehyde and 0.1% triton X100 in PBS for 3 minutes. The solution was removed by flicking the plate and blocking solution was added to the plate for 10 minutes. The blocking solution was removed by flicking the plate and the primary antibodies (rabbit anti-CD3ε (DAKO) and affinity purified rabbit anti-ζ (Oncoζ1) at 1:500 dilution were added to the appropriate wells and incubated at 4° C. for 1 hr.

Unbound antibodies were removed by flicking the plates and by washing the plate 3× with PBS using an automated microplate washer. A secondary antibody (biotinylated goat anti-rabbit IgG, 1:1000) was added to the wells and incubated for 30 min. at 4° C. The unbound secondary antibody was removed by washing the plate 3× with PBS using a microplate washer. Streptavidin-EuCl (Wallac, #1244-360, 1:1000 dilution) was added to each well and incubated for 10 min. at 40° C. The unbound streptavidin-EuCl was removed by washing the plate 3× with PBS using a microplate washer. To increase fluorescence, 100 μl of enhance solution (Wallac, #1244-105) was added to each well and incubated for 5 min. at room temperature. The fluorescence of each well was read in a time resolved fluorimeter (Wallac, Model #1232).

Table 3 illustrates that the ratios of CD3ζ to CD3ε (determined by cell-based immunoassay using time resolved fluorimetry) of several T cell populations were comparable to their ratios detected by the capture ELISA assay (See Example 2).

TABLE 3

Comparison of ζ/CD3ε Detection of Capture ELISA with Cell-Based Assay

| T cell | CD3ζ/CD3ε Ratios | |
|---|---|---|
| Populations* | ELISA ASSAY | CELL-BASED ASSAY |
| 1 | 1.2 | 1.2 |
| 2 | 1.0 | 0.9 |
| 3 | 1.4 | 1.1 |
| 4 | 1.2 | 1.3 |
| 5 | 1.4 | 1.6 |
| mean 1/2 SD | 1.2 ± 0.17 | 1.2 ± 0.25 |

*T cells were isolated from peripheral blood lymphocytes using R&D Systems' columns (HTCC-1000).

EXAMPLE 4

Conversion from TH1 to TH2 in Cancer

The amount of THl-type and TH2-type lymphokines present in serum of healthy, early TBM and later TBM was compared. Approximately $1 \times 10^6$ MCA-38 cells in 0.5 ml HBSS were injected subcutaneously in 6- to 8-week old C57BL/6 mice using a 30 gauge needle. Tumors grew progressively and mice were sacrificed at <14 or >26 days of tumor growth. The serum was collected and the spleen lymphocytes stimulated. The amount of IL-2, IFNγ, IL-4 and IL10 present in the serum of healthy untreated controls and MCA-38-treated mice was determined by ELISA.

Tumor-bearing mice exhibit a progressive loss in the ability to produce IL-2 and γIFN while at the same time producing increasingly more IL-4 and IL-10. There is an increase in the amount of IL-4 and IL-10 in the serum of MCA-38-treated mice that is not detectable in the normal healthy control mice. (Table 4). As the cancer develops in the MCA-38-treated mice there is a shift in the immune system from a TH-1 status to a TH-2 status.

TABLE 4

Increase in IL-4 and IL-10 in Mice with Tumors

| | IL-4* | IL-10** |
|---|---|---|
| Normal serum | 25 | 0.44 |
| Long-term tumors (32 days) | 30 | 2.35 |

*picograms/ml
**units/ml

EXAMPLE 5

Pattern of Protein Binding to an Oligonucleotide Probe Comprising the DNA Binding Region of a BRM Gene An electrophoretic mobility shift assay (EMSA) was used to compare the pattern of DNA binding found in nuclear extracts of TH-1 (AE.7) and TH-2 (D10.G41) mouse clones to that found in the nuclear extracts of splenic CD4+ T cells of normal mice and MCA-38-bearing mice at 11, 18 and 32 days after administration of MCA-38 cells to the animal. Nuclear extracts were prepared by pelleting cells at 1200 rpm for 5 min, washed once with cold phosphate buffered saline, and resuspended in lysis buffer (25 mM Hepes, pH 7.8, 50 mM KCl, 0.5% NP40 (v/v), 0.1 mM dithiothreitol) containing 1 mM PMSF and 1 μg/ml leupeptin and aprotinin A as protease inhibitors. Cells were lysed by incubating on ice for 5 min.

Lysates were centrifuged at 2000 rpm for 5 min, supernatant was collected as cytoplasmic extract, and the pellet was washed once with lysis buffer without NP40. The pellet was resuspended in elution buffer (25 mM Hepes, pH 7.8, 500 mM KCl, 10% glycerol (vv), 0.1 mM dithiothreitol) containing 1 mM PMSF, and 1 μg/ml leupeptin and aprotinin A. The resuspended pellet was gently mixed by using an end-to-end mixer for 20 min at 4° C. Supernatant was collected after centrifuging at 14000 rpm for 30 min, and was dialyzed for 2 h against dialysis buffer (25 mM Hepes, pH 7.8, 50 mM KCl, 10% glycerol, 0.1 mM DDT, and 1 mM PMSF). Aliquots were quickly frozen in dry ice/ethanol and stored at −70° C.

A $^{32}$P-labeled oligonucleotide corresponding to the sequence of the human γIFN gene promoter region was used as a probe. The nucleotide sequence of the oligonucleotide probe used was (SEQ ID NO:3)
5'AAAACTTGTGAAAATACGTAATCCTCAGGAGA 3'
The assay was done by pre-incubating nuclear extract (2 μg protein) in reaction buffer (10 μl total volume) containing 20 mM Tris (ph 7.5), 60 mM KCl, 4% Ficol, 2 mM EDTA, 0.5 mM DTT, 1 μg poly dIdC and with or without unlabeled competitors for 10 min at room temperature. The labelled oligonucleotide probe was then added to the reaction mixture and incubation continued for 20 min. The complexes were separated on a 4% polyacrylamide gel with 44.5 mM tris-borate (pH 8.3) and 1 mM EDTA buffer. After electrophoresis, the gel was dried and exposed to autoradiography.

Nuclear extracts (2 μg protein) from TH-1 and TH-2 clones were used in the assay. The competitor (100-fold molar excess) consisted of unlabeled oligonucleotide. Nuclear extracts (2 μg protein) from splenic CD4+ T cells of normal mice and mice bearing MCA-38 for 18 and 32 days were assayed in the same manner as the TH-1 and TH-2 nuclear extracts. Competitors (100-fold molar excess) used were unlabeled specific and non-specific oligonucleotides.

In the DNA-binding assay using nuclear extracts from TH-1 cells, two specific DNA-protein complexes were obtained (Bands 1 and 2). Bands 1 and 2 were drastically reduced in the nuclear extract of TH-2 cells. Moreover, a new DNA-protein complex was observed in the TH-2 nuclear extract which was absent in TH-1 (Band 3).

Nuclear extracts (2 μg protein) from splenic CD4+ T cells of normal mice and mice bearing MCA-38 for 11, 18 and 32 days were assayed in the same manner as the TH-1 and TH-2 nuclear extracts. Two DNA-protein complexes were observed in the nuclear extracts from normal control mice that correspond to bands 1 and 2 of TH-1 cells. Bands 1 and 2 progressively decreased in day 11, 18 and 32 MCA-38 tumor-bearing mice. A third DNA-protein complex was observed in day 11 tumor-bearing mice that corresponded to band 3 in the TH-2 cells. However, band 3 progressively decreased in day 18 and day 32 tumor-bearing mice. Therefore the pattern of protein binding to an oligonucleotide probe that comprises a diagnostically significant portion of the protein binding region of the γIFN gene in MCA-38 tumor-bearing mice is neither equivalent to the TH-1-type pattern of protein binding observed in normal control mice nor equivalent to the TH-2-type pattern of TH-2 cells and therefore is characterized as TH-2'.

Accordingly, the pattern of protein binding to an oligonucleotide probe that comprises all or a diagnostically significant portion of the protein binding region of a gene for a BRM can be used to identify patients having an altered immune status.

EXAMPLE 6

Methylation Status of Nucleotides Within Regulatory Element of BRM Gene

The mouse TH-1 clone D1.1 and the mouse TH-2 clone CDC25 were obtained from Dr. Abul Abbas (Harvard Medical School) and Dr. David Parker (Univ. of Massachusetts), and are specific for rabbit gamma globulin in the context of IA$^d$. The derivation of the TH-2 cell line D10.G41, obtained from the American Type Culture Collection (Rockville, Md.) has been described. Kaye (1983). Clone A.E7, a murine TH-1 clone, was obtained from Dr. Ronald Schwartz, NIH, and is specific for pigeon cytochrome c, H-2$^k$. Clone LV3M (TH-1) was obtained from Dr. Louis Rizzo, National Eye Institute, and is specific for KLH, H-2$^d$. Clones B10 (TH-1); 2A11 (TH-2); and A109.1 (TH-2) are specific for Staphenterotoxin B (SEB), H-2$^b$; (SEB/KLH, H-2$^d$; and SEB, H-2$^d$; respectively. All mouse T cell clones were stimulated every 2 weeks and rested for 7–10 days after stimulation before use.

Human CD4 clones AD-14 and AD-20 were isolated by direct limiting dilution cloning of peripheral blood CD4 T cells from healthy adult donors. CD4 T cells were isolated from peripheral blood. Lewis (1988). The CD4 T cells were seeded at 1 or 5 cells per well into 96-well round bottom plates that contained 10×10$^5$ irradiated adult peripheral blood mononuclear cells (3000 rad) in CT.4S medium (Hu-Li (1989)), supplemented with 3.1 µg/ml Con A (Pharmacia, Piscataway, N.J.), 0.5 ng/ml PMA (Sigma, St. Louis, Mo.), purified human IL-2, 5 U/ml (Boehringer-Mannheim), and 5 ng/ml recombinant human IL-2, kindly provided by Dr. Ken Grabstein, (Immunex Corp). overlying medium (0.1 ml) was replaced with an equal volume of fresh IL-2 (5 U/ml, Boehringer-Mannheim) containing medium every 3–5 days. Growth positive wells were scored macroscopically at 3 wk and expanded in 12-well tissue culture plates by stimulation with Con A, IL-2 and feeder cells every 2–3 wk.

For γIFN production analysis, cells were cultured at 1×10$^6$/ml in RPMI medium supplemented with 2 mM L-glutamine and 10% FCS and stimulated with 25 µl of Con A (Pharmacia) for 24 h. Supernatants were collected and frozen at −80° C. until assayed for cytokine content by ELISA. Thymocytes were isolated by Ficoll® Hypaque® centrifugation from infants undergoing cardiac surgery. Lewis (1991).

DNA from murine cells was extracted using guanidinium isothiocyanate. Pange (1992). DNA was extracted from human cells using proteinase K (200 µg/ml) digestion followed by phenol-chloroform extraction. Murine genomic DNA (5 or 7.5 µg) was digested with 50 units of BamH 1 and 25 units of SnaB 1, or 50 units of BamH 1 followed by isopropanol precipitation and overnight digestion with either Mspl or HpaII. Human genomic DNA (10 µg) was digested with 50 units of PvuII and 25 units of SnaB 1 (all restriction enzymes from Boehringer Mannheim). After digestion overnight at 37° C. in Boehringer-Mannheim M buffer, the DNA was subjected to agarose gel electrophoresis, transferred to Magnagraph nylon membranes (MSI, Westboro, Mass.), UV crosslinked and baked of 1 h at 80° C. Murine and human DNA blots were hybridized with Nylohybe hybridization buffer (Digene, Inc., Silver Spring, Md.) according to the manufacturer's instructions. For Southern blots of murine DNA, the probe consisted of the full length murine γIFN cDNA. For human DNA blots, the probe consisted of a HindIII/SauI human γIFN genomic fragment that includes the first exon segment. Gray (1982).

EMSA was performed under standard conditions. Norihisa (1994). For methylation studies, the $^{32}$P-labeled oligonucleotide was incubated with CpG methylase (New English Biolabs) as recommended by the manufacturer.

The murine TH-1 clone A.E7 and TH-2 clone D10.G41 were transfected by electroporation utilizing a BioRad electroporation device at 270 volts, 960 microfarads. Forty micrograms of DNA was utilized with 20×10$^6$ cells. After electroporation, cells were rested overnight, then stimulated 24 h with plate bound anti-CD3. CAT activity was measured by the liquid scintillation CAT assay after 48 h Lederer (1994).

Cell culture supernatants were analyzed for mouse γIFN utilizing a commercially available ELISA (Endogen, Minneapolis, Minn.) by Clinical Immunology Services, PRI/DynCorp, NCI-FCRDG. For measurement of human γIFN by ELISA, plates were coated with 5 µg/ml murine anti-human γIFN mAb 20B8 (provided by Genentech, South San Francisco, Calif.) in 0.05 carbonate buffer (pH9.6) for 12–24 h at 4° C. and blocked with PBS with 0.5% BSA and 0.05% Tween-20 (EIA buffer). Samples were applied to wells for 2 h at room temperature. Plates were sequentially incubated with rabbit anti-rhγIFN serum (1:10,000 in EIA buffer) (Genentech, South San Francisco, Calif.) for 1 h, horseradish peroxidase-conjugated goat anti-rabbit Ig (1:5000 in EIA buffer, TAGO, Burlingame, Calif.). Wells were developed by addition of TMB substrate solution as directed by the manufacturer (Kirkegaard and Perry, Gaithersburg, Md.), and after 30–60 min O.D. 650 was determined using a plate reader. TH-1 clones selectively produced γIFN and IL-2 while TH-2 clones selectively produced IL-4 and IL-5.

Southern blot analysis of murine T helper clones revealed the following. A SnaB 1 site lies just proximal to the first exon of the γIFN gene and if the DNA is cut by BamH 1 and SnaB 1, a 5 kb DNA fragment should be revealed by Southern blot analysis using the γIFN cDNA as a hybridization probe. DNA from each of the TH-1 and TH-2 clones was cut with BamH 1 alone revealing the expected 10 kb γIFN genomic DNA. Gray (1982). DNA was extracted from the TH-1 clones D1.1 and A.E7 and was completely cut by SnaB 1. Only a single band is present because the probe used for the hybrizaiton was the murine γIFN cDNA that does not hybridize to the 5-prime flank. DNA was isolated from TH-2 clones D10 and CDC25 and was not cut by SnaB 1, indicating that the enzyme site is methylated in the TH-2 clones. Restriction enzyme analysis of two additional independently isolated TH-1 clones (B10 and LV3M) produce the same restriction pattern as TH-1 clones D1.1 and A.E7. Restriction enzyme analysis of two additional independently isolated TH-2 clones (A109.1 and 2A11) produced the exact same restriction enzyme pattern as TH-2 clones D10.g41 and CDC25. Accordingly, Southern blot analysis revealed a correlation between the hypomethylation of the SnaB 1 site and γIFN expression.

In an effort to determine if other sites within the γIFN genomic DNA were also hypomethylated in TH-1 cells, DNA from two TH-1 clones and two TH-2 clones were digested with BamH 1 and Mspl or Hpa II (CCGG recognition site). These sites are not located in introns and 5' HpaII sites are approximately 1200 bp and 2600 bp upstream of the transcription initiation site. The DNA from the TH-1 clones D1.1 and AE7 was digested differently by Hpa II than the DNA from the TH-2 clones D10.G41 and CDG25. The band pattern indicates that sites far upstream of the promoter (most likely −2600) were hypomethylated in TH-2 cells but not in the TH-1 cells. In addition, the 0.5 kb band present in HpaII digests of TH-1 but not TH-2 DNA indicates that at least 2 or 3 sites at the 3' end of the gene were hypomethylated in TH-1 but not TH-2 cells. The presence of a 2–3 kb band in the digestion could not be readily explained, but may reflect the presence of an Msp/HpaII site in the third intron not predicted from the published murine IFN-γ genomic sequence or present in the genomic DNA clone. Thus, hypomethylation of the entire γINF genomic DNA does not occur in TH-1 cells and TH-1 and TH-2 cell lines exhibit specific methylation differences.

Southern blot analysis of human T lymphocyte clones was undertaken to determine if hypomethylation of the SnaB 1 site also correlated with γIFN gene expression in two adult $CD4^+$ human T-cell clones AD-14 and AD-20. Total genomic DNA was isolated from the $CD4^+$ clones and human thymocytes. The thymocyte DNA digested with either PvuII or PvuII and SnaB 1 produced a single band of 6.7 kb when probed with the HindIII/SauI human γIFN genomic fragment that includes the first exon segment. Digestion of AD-14 DNA with PvuII and SnaB 1 produced a single band of 2.6 kb. Digestion of AD-20 DNA with PvuII and SnaB 1 followed by hybridization with the HindII/Sau I fragment produced 2 bands measuring 2.6 and 6.7 kb. Accordingly, the CD4+ human T cell clones were cleaved by SnaB 1 and this is consistent with the ability of these cells to produce γIFN mRNA. Protein analysis after 24 h stimulation with anti-CD3 antibody resulted in 3890 pg/ml and 69 pg/ml of γIFN from clones AD-14 and AD-20 but less than 20 pg/ml from whole thymocytes, demonstrating a rough correlation between levels of γIFN produced and extent of SnaB 1 cleavage.

Based on these results, it was next determined if specific DNA-protein complexes could be formed with an oligonucleotide containing this methylation site and if methylation in vitro might affect the ability of DNA binding proteins to interact with this site in the γIFN promoter. The EMSA assays were performed using nuclear extracts from the murine TH-1 clone D1.1.

A $^{32}$P-labeled oligonucleotide corresponding to the sequence of the γIFN gene promoter region was used as a probe. The nucleotide sequence of the oligonucleotide probe used was (SEQ ID NO:3)
5'AAAACTTGTGAAAATACGTAATCCTCAGGAGA 3'
This is the −71 to −40 region of the human γIFN promoter. This region is identical to that of the mouse promoter (−69 to −40) with one important difference. The mouse promoter contains an additional CpG dinucleotide at positions −48 and −47 while the human promoter contains a TC at this location. Thus, by using the human promoter, the only CG dinucleotide in the oligonucleotide is in the SnaB 1 site.

At least five specific complexes were observed with an oligomer containing the γIFN SnaB 1 site in the D1.1 nuclear extracts. These complexes appeared to be specific as loss of binding was observed when cold oligonucleotide was added as the competitor, but not when an oligonucleotide containing an Sp1 site was added as the competitor. Treatment of the cells with anti-CD3 bound to plates for 18 h did not result in any increase in the levels or numbers of complexes. In addition, mutation of the C to T results in decreased levels of three of the complexes indicating that the C plays a role in the formation of these complexes.

Bands 1–4 observed in the nuclear extracts of the D1.1 cells apparently correspond to bands 1–3 observed in the TH-1 (AE.7) and TH-2 (D10.G41) mouse clones because bands 2 and 3 of the D1.1 cells appear to be a doublet of band 2 of the AE.7 and D10.G41 cells. The difference in the protein binding pattern between TH-1 clones D1.1 and AE.7 may be the result of cell culturing.

In order to determine if methylation of the CpG affected the protein complexes, the oligonucleotide was methylated in vitro utilizing a commercially available CpG methylase. Specific binding in 3 of the 5 complexes was lost after methylation. However, not all complexes were lost indicating that this specific methylation did not totally block all protein interaction with the oligonucleotide. This inhibition was not the result of the methylase binding to the DNA as, in a mock reaction in which the S-adenosylmethionine was omitted, no loss of DNA-protein complex formation as observed.

As these results suggest that introduction of a non-methylated γIFN promoter into a TH-2 cell line might result in transcriptional activity, the full length γIFN promoter linked to the CAT gene was transiently transfected into the TH-1 clone A.E7 and the TH-2 clone D10.G41. Transfection into A.E7 resulted in CAT activity almost 3-fold higher than seen with the pCAT vector alone, and this activity was not increased by anti-CD3 treatment of the cells. This same plasmid was very weakly active and also not inducible upon transfection into the TH-2 clone D10.G41. As this DNA is unlikely to become methylated in a transient transfection assay, these results are consistent with the hypothesis that in addition to methylation differences, TH-2 cells may have quantitative and/or qualitative differences in specific DNA binding proteins as compared to TH-1 cells and that additional proteins and regulatory regions may be required for inducible γIFN gene expression.

It was previously shown that treatment with 5-azacytidine of a murine T-cell line and Hut78 cells resulted in these cells reacquiring the capacity to produce γIFN. Farrar (1985). Hardy (1985). To determine if inhibition of DNA methylation in the TH-2 cells could result in an activation of γIFN gene expression, two TH-2 clones were treated with anti-CD3 prior to, or after treatment with, 5-azacytidine and culture supernatants were analyzed for γIFN by ELISA. The 5-azacytidine treatment did result in anti-CD3 induced expression of γIFN by the clones after 48 h, consistent with the hypothesis that methylation of specific regions of the genomic DNA is involved in the control of γIFN mRNA expression. The production of γIFN by one of the clones was comparable to that observed with TH-1 cells treated with anti-CD3.

Methylation of specific regions of the DNA is an important mechanism for the control of γIFN gene expression in T lymphocytes. Indeed, if TH-O cells, which express γIFN, are precursors of TH-1 and TH-2 cells, the data indicate that remethylation of the promoter of the γIFN gene is triggered by an as yet unknown mechanism during the differentiation process towards a TH-2 phenotype. These findings do not imply that methylation or the lack of methylation of DNA at the SnaB 1 site and/or other sites in the YIFN gene is the only mechanism by which the potential for γIFN expression in T cells is controlled. There are multiple regions in the promoter and first intron of the γIFN gene that contribute to control of tissue-specific and activation-specific expression.

The failure to observe increased CAT activity in the TH-1 clone, A.E7, after anti-CD3 treatment suggests strongly that other regions, perhaps intronic, also are required for full promoter activity. Demethylation of specific regions of the gene may be a necessary event that permits accessibility of basal regulatory proteins, permitting enhanced gene expression after addition DNA binding proteins are induced by T-cell activation. Additionally, demethylation may activate expression of transcription factors encoded outside of the γIFN genetic locus required for maximal γIFN gene expression. The observation that TH-2 cells contain higher levels of one of the protein complexes than observed in TH1 cells suggest that possibly additional or modified proteins, including transcriptional repressors, may bind to specific regions of the promoter and inhibit transcription.

Accordingly, a method of identifying patients having an altered immune status comprises determining, in a lymphocyte preparation from a patient being evaluated, the methylation status of nucleotides within the regulatory element of a BRM gene; and determining, in a lymphocyte preparation from one or more healthy individuals, the methylation status of nucleotides within said regulatory element of a BRM gene. The methylation status in the patient's lymphocyte preparation is compared to said methylation status in the healthy individual's lymphocyte preparation and a significant variation thereof is an indication of an altered immune status in said patient.

EXAMPLE 7

Density Gradient Assay

Human peripheral blood lymphocytes were obtained by methods well known in the art. The red blood cells in a sample of peripheral flood were lysed in SCK buffer and the cell debris removed by means of centrifugation. The remaining cells were placed over a discontinuous Percolli gradient prepared in the following manner. Each fraction of the gradient is prepared in RPMI 1640 supplemented with 2% Fetal Calf Serum, glutamine, penicillin, streptomycin and 5mM Hepes. The osmolarity of the medium is adjusted to 280 to 285 mOsm/kg $H_2O$. The osmolarity of the Percolls is adjusted to 285 mOsm/kg $H_2O$ with 10× concentrated PBS. The gradient is prepared in Falcon 2095 15 ml conical test tubes as follows:

| Medium (μl) | Fraction | Percoll ® (μl) | Volume (ml) |
|---|---|---|---|
| 3,550 | 1 | 2,450 | 2.5 |
| 3,440 | 2 | 2,660 | 2.5 |
| 3,250 | 3 | 2,750 | 2.5 |
| 3,100 | 4 | 2,900 | 1.5 |
| 2,950 | 5 | 3,050 | 1.5 |
| 2,800 | 6 | 3,200 | 1.5 |
| 2,000 | 7 | 4,000 | 1.5 |

The refractive Index at 25° C. of fractions 1, 2, 3, 4, 5, 6, and 7 is 1.3432, 1.3436, 1.3440, 1.3443, 1.3446, 1.3450 and 1.3470, respectively.

$50 \times 10^6$ cells were carefully layered on top of the gradient to avoid mixing, and the tubes were centrifuged at 550 g for 30 min. at room temperature in a Beckman TJ-6 table centrifuge.

Following centrifugation, six discrete bands were observed. T lymphocytes from healthy individuals were predominantly found in Fraction 6 (F6), although a small number of T lymphocytes were found in Fraction 3 (F3). Monocytes are predominately found in Fraction 1 (F1) and NK cells and LGLs are predominately found in Fraction 2 (F2).

The F6 cells were stimulated with anti-CD3 antibody for 1 h and the nuclear proteins in the stimulated cells were analyzed. The proteins p65 and c-Rel were detectable in the nucleus of stimulated F6 cells but not in unstimulated F6 cells. An increased amount of p50 protein was detectable in the nucleus of stimulated F6 cells compared to unstimulated F6 cells.

In contrast, the T lymphocytes from human melanoma and renal cell carcinoma patients were predominantly found in F3 following density gradient centrifugation in Percoll® under the same conditions. The F6 T lymphocytes were stimulated with anti-CD3 for 1 h. The proteins p65 and c-Rel were not detectable in the nucleus of stimulated F6 cells from these patients. Likewise, there was no increase in the amount of p50 in the nucleus of stimulated F6 cells from the patients.

Accordingly, an immune status index is the pattern of distribution of T lymphocytes in a density gradient. More specifically, an immune status index is the ratio of T lymphocytes in F3 to F6, as measured by cell number or total protein. A change in the pattern of distribution of T lymphocytes in the density gradient, or in the F3/F6 ratio in the patient, compared to healthy coqtrols, is diagnostic of a change in the immune status index of the patient.

Cited Documents

The references listed below are incorporated herein by reference to the extent that they supplement, explain, provide a background for, or teach methodology, techniques, and/or compositions employed herein.

Baeuerle, P. A., *Biophysica Acta* 1072: 63–80 (1991).

Berridge, C. B. et al., *Nature* 341: 197 (1989).

Blumberg, R. S. et al., *Proc. Natl. Acad. Sci. USA* 87: 7220 (1990).

Coligan, J. E., Vol. I. *Current Protocols in Immunology*, Green Publishing Associates and Wiley-Interscience, 2.4.1–2.10.3 (1991).

Farrar et al., *J. Immunol.* 135: 1551 (1985).

Gray et al., *Nature* 298: 859 (1982).

Hardy et al., *Proc. Natl. Acad. Sci. USA* 82: 8173 (1985).

Hsi, E.D. et al., *J. Biol. Chem.* 264: 10836 (1989).

Hm-Li et al., *J. Immunol.* 42: 800 (1989).

Imboden, J. B. et al., *J. Exp. Med.* 161: 446 (1985).

June, C. H. et al., *J. Immunol.* 144: 1591 (1990).

Kaye et al., *J. Exp. Med.* 158: 836 (1983).

Klausner, R. D., *New Biol.* 1: 3 (1989).

Klausner, R. D. et al., *Annu. Rev. Cell Biol.* 6: 403 (1990).

Klausner, R. D. et al., *Cell* 64: 875 (1991).

Koning, F. et al., *Eur. J. Immunology* 20: 299 (1990).

Lederer et al., *J. Immunol.* 152: 77 (1994).

Lewis et al., *Proc. Natl. Acad. Sci. USA* 85: 974 (1988).

Mizoguchi et al., *Science* 258: 1795 (1992).

Munoz et al., *Proc. Natl. Acad. Sci. USA* 86: 9461 (1989).

Norihisa et al., *J. Immunol.* 152: 485 (1994).

Novak et al., *Proc. Natl. Acad. Sci. USA* 87: 9353 (1990).

Patel, M. D. et al., *J. Biol. Chem.* 262: 5831 (1987).

Pang et al. *Blood* 80: 724 (1992).

Samelson, L. E. et al., *Cell* 46: 1083 (1986).

Samelson, L. E. et al., *Proc. Natl. Acad. Sci. USA* 87: 4358 (1990).

Sites, D. P. et al., Chapter 22 of *Basic and Clinical Immunology* 4th ed. Lange Medical Publications of Los Altos, Calif. (1982).

Weiss, A. et al., *Proc. Natl. Acad. Sci. USA* 81: 4169 (1984).

U.S. Pat. No. 5,246,831

We claim:

1. A method of identifying patients having an altered immune status, said method comprising the steps of:
   a. determining, in a lymphocyte preparation from a patient being evaluated, the pattern of protein binding to an oligonucleotide probe that comprises all or a diagnostically significant portion of the protein binding region of a gene for a BRM;
   b. determining, in a lymphocyte preparation from one or more healthy individuals, the pattern of protein binding to an oligonucleotide probe that comprises all or a diagnostically significant portion of the protein binding region of said gene for a BRM; and
   c. comparing said pattern of protein binding to said oligonucleotide probe in the patient's lymphocyte preparation, to said pattern of protein binding to said oligonucleotide probe in the healthy individual's lymphocyte preparation, a significant variation thereof being an indication of an altered immune status in said patient.

2. The method of claim 1, wherein said BRM is selected from the group consisting of γIFN, IL-2, IL-4, IL-5, IL-6, IL10 and IL12.

3. The method of claim 1, wherein said lymphocyte preparation is prepared from fluid or tissue selected from the group consisting of spleen tissue, peripheral blood, tumor tissue, lymph node tissue, cerebrospinal fluid, pleural effusions and ascites.

4. The method of claim 2, wherein said oligonucleotide probe has the DNA sequence 5'AAAACTTGT-GAAAATACGTAATCCTCAGGAGA 3' (SEQ ID NO:3).

5. The method of claim 1, wherein said BRM is a TH1-type BRM.

6. The method of claim 1, wherein said BRM is γIFN.

7. The method of claim 1, wherein said BRM is a TH2-type BRM.

8. The method of claim 1, wherein said BRM is a TH2'-type BRM.

9. The method of claim 1, wherein said determining steps comprise an electrophoretic mobility shift assay.

10. The method of claim 1, wherein steps (a) and (b) each additionally comprise subjecting a lymphocyte preparation to density gradient centrifugation, and step (c) additionally comprises comparing density gradients obtained in steps (a) and (b), a significant variation in density gradients being a further indication of an altered immune status in said patient.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 14 amino acids
       (B) TYPE: amino acid
       (D) TOPOLOGY: linear (ii) MOLECULE TYPE: peptide (xi) SEQUENCE DESCRIPTION: SEQ ID NO:1:

Arg Arg Arg Gly Lys Gly His Asp Gly Leu Tyr Gln Gly Cys
1               5                   10

(2) INFORMATION FOR SEQ ID NO:2:

(i) SEQUENCE CHARACTERISTICS:
       (A) LENGTH: 15 amino acids
       (B) TYPE: amino acid
       (D) TOPOLOGY: linear (ii) MOLECULE TYPE: peptide (xi) SEQUENCE DESCRIPTION: SEQ ID NO:2:

Asp Thr Tyr Asp Ala Leu His Met Gln Thr Leu Ala Pro Arg Cys
1               5                   10                  15

(2) INFORMATION FOR SEQ ID NO:3:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

AAAACTTGTG AAAATACGTA ATCCTCAGGA GA                                          32